US008889360B2

(12) United States Patent
Saito et al.

(10) Patent No.: US 8,889,360 B2
(45) **Date of Patent: *Nov. 18, 2014**

(54) THERMAL CYCLER AND THERMAL CYCLING METHOD

(71) Applicant: Seiko Epson Corporation, Tokyo (JP)

(72) Inventors: Yuji Saito, Matsumoto (JP); Fumio Takagi, Chino (JP)

(73) Assignee: Seiko Epson Corporation (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/060,132

(22) Filed: Oct. 22, 2013

(65) Prior Publication Data

US 2014/0045255 A1 Feb. 13, 2014

Related U.S. Application Data

(63) Continuation of application No. 13/297,747, filed on Nov. 16, 2011, now Pat. No. 8,592,160.

(30) Foreign Application Priority Data

Nov. 17, 2010 (JP) ................................ 2010-256545

(51) Int. Cl.

*C12Q 1/68* (2006.01)
*C12P 19/34* (2006.01)
*B01L 7/00* (2006.01)
*B01L 3/00* (2006.01)

(52) U.S. Cl.

CPC ........... *B01L 7/52* (2013.01); *B01L 2400/0457* (2013.01); *B01L 2400/0409* (2013.01); *B01L 7/525* (2013.01); *B01L 3/5082* (2013.01); *B01L 2300/1872* (2013.01)

USPC ........................... 435/6.12; 435/6.1; 435/6.11

(58) Field of Classification Search

None

See application file for complete search history.

(56) References Cited

U.S. PATENT DOCUMENTS 8,592,160 B2 * 11/2013 Saito et al. .................. 435/6.12

FOREIGN PATENT DOCUMENTS

JP 2009-136250 A 6/2009

OTHER PUBLICATIONS

Williams et al., "Amplification of complex gene libraries by emulsion PCR," Nature Methods, Jul. 2006, vol. 3, No. 3, pp. 545-550.*

* cited by examiner

*Primary Examiner* — Young J Kim

(74) *Attorney, Agent, or Firm* — Harness, Dickey & Pierce, P.L.C.

(57) ABSTRACT

A thermal cycler includes a holder to which a biotip having a longitudinal direction is attached in such a manner that one end portion of the biotip is at a higher level than the other end portion, and that the distance between one end portion of the biotip and the rotational axis is shorter than the distance between the other end portion of the biotip and the rotational axis, a heating unit heats a first end portion of the biotip, a rotating unit rotates the holder, and a controller that controls the rotation speed of the rotating unit. The controller has a first mode a rotation speed at which the magnitude of the centrifugal force acting on the reaction mixture becomes smaller than the gravity, and a second mode a rotation speed at which the magnitude of the centrifugal force acting on the reaction mixture becomes greater than the gravity.

7 Claims, 7 Drawing Sheets

THERMAL CYCLER AND THERMAL CYCLING METHOD

CROSS-REFERENCE TO RELATED APPLICATIONS

This is a continuation application of U.S. application Ser. No. 13/297,747 filed Nov. 16, 2011, which claims priority to Japanese Patent Application No. 2010-256545, filed Nov. 17, 2010, all of which are hereby incorporated by reference in their entireties.

BACKGROUND

1. Technical Field

The present invention relates to thermal cyclers and thermal cycling methods.

2. Related Art

Recent studies revealed genes involved in a wide range of diseases, and there is growing interest in remedies that use genes, such as in gene diagnosis and gene therapy. Manly techniques that use genes for variety discrimination and breeding also have been developed in the field of agriculture and livestock. One widely used technique that makes use of genes is the nucleic acid amplification technique. A commonly known example of the nucleic acid amplification technique is PCR (Polymerase Chain Reaction). PCR is a technique used to amplify the target nucleic acid in the thermal cycling of a solution (reaction mixture) that includes a nucleic acid to be amplified (target nucleic acid) and reagents. The thermal cycling is the process by which the reaction mixture is periodically subjected to two or more stages of temperature. Thermal cycling that involves two or three stages is commonly used in PCR. PCR has become a technique indispensable for understanding the information of biological substances.

PCR generally uses a biochemical reaction chamber called a tube or a biotip (biological sample reaction tip). However, the techniques of related art are problematic, because the reaction uses large amounts of reagents and other materials, and is time consuming. The reagents used for PCR are generally expensive, and should desirably be used in as small an amount as possible. Further, a reactor capable of performing PCR in a short time period is needed for, for example, the diagnosis of infections. As a solution to these problems, JP-A-2009-136250 discloses a biological sample reactor with which thermal cycling is performed by moving a reaction mixture while a biotip charged with the reaction mixture and a liquid immiscible with the reaction mixture and having a smaller specific gravity than the reaction mixture (such as mineral oil; hereinafter, such liquids will be referred to simply as “liquid”) is rotated about a horizontal rotational axis.

In the biological sample reactor disclosed in JP-A-2009-136250, the biotip is continuously rotated to perform a thermal cycle for the reaction mixture. Because the reaction mixture moves within the channel of the biotip as the biotip rotates, the biotip needs to be devised by, for example, making a complicated channel structure, in order to maintain the reaction mixture at a desired temperature for a desired time period.

SUMMARY

An advantage of some aspects of the invention is to provide a thermal cycler and a thermal cycling method with which the heating time can be easily controlled.

Application Example 1

A thermal cycler according to this Application Example includes: a holder to which a biotip is attached, the biotip having a longitudinal direction, and being charged with a reaction mixture and a liquid immiscible with the reaction mixture and having a smaller specific gravity than the reaction mixture; a heating unit that heats a first end portion at an end of the longitudinal direction of the biotip attached to the holder; a rotating unit that rotates the holder; and a controller that has a first mode and a second mode, the first mode being a setting in which the rotation speed of the rotating unit is set to a first speed at which the magnitude of the centrifugal force that acts on the reaction mixture by the rotation of the rotating unit is smaller than the magnitude of the gravitational force that acts on the reaction mixture, the second mode being a setting in which the rotation speed of the rotating unit is set to a second speed at which the magnitude of the centrifugal force that acts on the reaction mixture by the rotation of the rotating unit is greater than the magnitude of the gravitational force that acts on the reaction mixture. The biotip is attached to the holder in such a direction that a distance between the first end portion of the biotip and the rotational axis of the rotating unit is shorter than a distance between the rotational axis and a second end portion representing an end of the longitudinal direction of the biotip and different from the first end portion, and that a gravitational potential of the first end portion is smaller than a gravitational potential of the second end portion.

The thermal cycler according to this Application Example has the first mode in which the rotation speed of the rotating unit is set to a first speed, and the second mode in which the rotation speed of the rotating unit is set to a second speed different from the first speed. The first speed is a speed at which the magnitude of the centrifugal force that acts on the reaction mixture is smaller than the gravitational force that acts on the reaction mixture. The second speed is a speed at which the magnitude of the centrifugal force that acts on the reaction mixture is greater than the gravitational force that acts on the reaction mixture. The distance between the first end portion in the longitudinal direction of the biotip attached to the holder and the rotational axis of the rotating unit is shorter than the distance between the rotational axis and the second end portion representing an end of the longitudinal direction of the biotip and different from the first end portion. Further, the biotip is attached in such a direction that the gravitational potential of the first end portion is smaller than the gravitational potential of the second end portion. Specifically, because the gravitational force exceeds the centrifugal force in the first mode, the gravitational force acting on the reaction mixture holds the reaction mixture at the first end portion where the gravitational potential is smaller than at the second end portion. On the other hand, in the second mode, the centrifugal force exceeds the gravitational force, and thus the centrifugal force acting on the reaction mixture holds the reaction mixture at the second end portion situated farther away from the rotational axis than the first end portion. The reaction mixture held at the first end portion in the first mode can then be maintained at a predetermined temperature by heating the first end portion with the heating unit. Because the second end portion is farther away from the rotational axis than the first end portion, the first end portion and the second end portion have different temperatures. Specifically, the temperature of the reaction mixture held at the second end portion in the second mode can be maintained at a different temperature from that of the first end portion. The thermal cycler can thus easily control the heating time by controlling the rotation time in the first mode and the second mode.

Application Example 2

The thermal cycler according to the foregoing Application Example may further include a second heating unit that heats the second end portion, wherein the heating unit heats the first end portion to a first temperature, and wherein the second heating unit heats the second end portion to a second temperature different from the first temperature.

Because the thermal cycler according to this Application Example includes the second heating unit that heats the second end portion to the second temperature, the temperature of the second end portion of the biotip attached to the holder can be more accurately controlled. This improves the accuracy of the thermal cycling performed for the reaction mixture.

Application Example 3

A thermal cycling method according to this Application Example is a thermal cycling method that uses a thermal cycler. The method includes: attaching a biotip to the thermal cycler, the biotip having a longitudinal direction, and being charged with a reaction mixture and a liquid immiscible with the reaction mixture and having a smaller specific gravity than the reaction mixture; heating a first end portion at an end of the longitudinal direction of the biotip; rotating the biotip at a first speed about a predetermined rotational axis; and rotating the biotip at a second speed different from the first speed about the predetermined rotational axis. The biotip is attached in such a direction that a distance between the first end portion and the predetermined rotational axis is shorter than a distance between the predetermined rotational axis and a second end portion representing an end of the longitudinal direction of the biotip and different from the first end portion, and that a gravitational potential of the first end portion is smaller than a gravitational potential of the second end portion.

The thermal cycling method of this Application Example includes rotating the biotip at a first speed, and rotating the biotip at a second speed different from the first speed. The first speed is a speed at which the magnitude of the centrifugal force that acts on the reaction mixture is smaller than the gravitational force that acts on the reaction mixture. The second speed is a speed at which the magnitude of the centrifugal force that acts on the reaction mixture is greater than the gravitational force that acts on the reaction mixture. The biotip is attached to the thermal cycler so that the distance between the first end portion in the longitudinal direction of the biotip and the rotational axis of the rotating unit is shorter than the distance between the rotational axis and the second end portion representing an end of the longitudinal direction of the biotip and different from the first end portion. Further, the biotip is attached in such a direction that the gravitational potential of the first end portion is smaller than the gravitational potential of the second end portion. Specifically, rotating the biotip at the first speed holds the reaction mixture at the first end portion where the gravitational potential is smaller than at the second end portion, because the reaction mixture is acted upon by the gravitational force that exceeds the centrifugal force. On the other hand, rotating the biotip at the second speed makes the centrifugal force higher than the gravitational force, and thus the reaction mixture, by being acted upon by the centrifugal force, is held at the second end portion farther away from the rotational axis than the first end portion. The temperature of the reaction mixture held at the first end portion as a result of rotating the biotip at the first speed can be maintained at a predetermined temperature by heating the first end portion. On the other hand, the temperature of the second end portion becomes different from that of the first end portion, because the second end portion is farther away from the rotational axis than the first end portion. Specifically, the temperature of the reaction mixture held at the second end portion as a result of rotating the biotip at the second speed can be maintained at a different temperature from that of the first end portion. The thermal cycling method can thus easily control the heating time by controlling the rotation time of the biotip at the first speed and the second speed.

Note that the configurations above can be combined within the limits of the gist of the invention.

BRIEF DESCRIPTION OF THE DRAWINGS

The invention will be described with reference to the accompanying drawings, wherein like numbers reference like elements.

DESCRIPTION OF EXEMPLARY EMBODIMENTS

The following describes preferred embodiments of the invention with reference to the accompanying drawings, in the order below. It should be noted that the embodiments described below do not unduly restrict the substance of the invention recited in the claims. Note also that the configurations described below do not necessarily represent the necessary constituting elements of the invention.

1. Embodiment
    1-1. Configuration of thermal cycler
    1-2. Thermal cycling using thermal cycler
2. Variations
    2-1. Variation 1
    2-2. Variation 2
    2-3. Variation 3
    2-4. Variation 4

1. Embodiment 1-1. Configuration of Thermal Cycler

Figure 1:
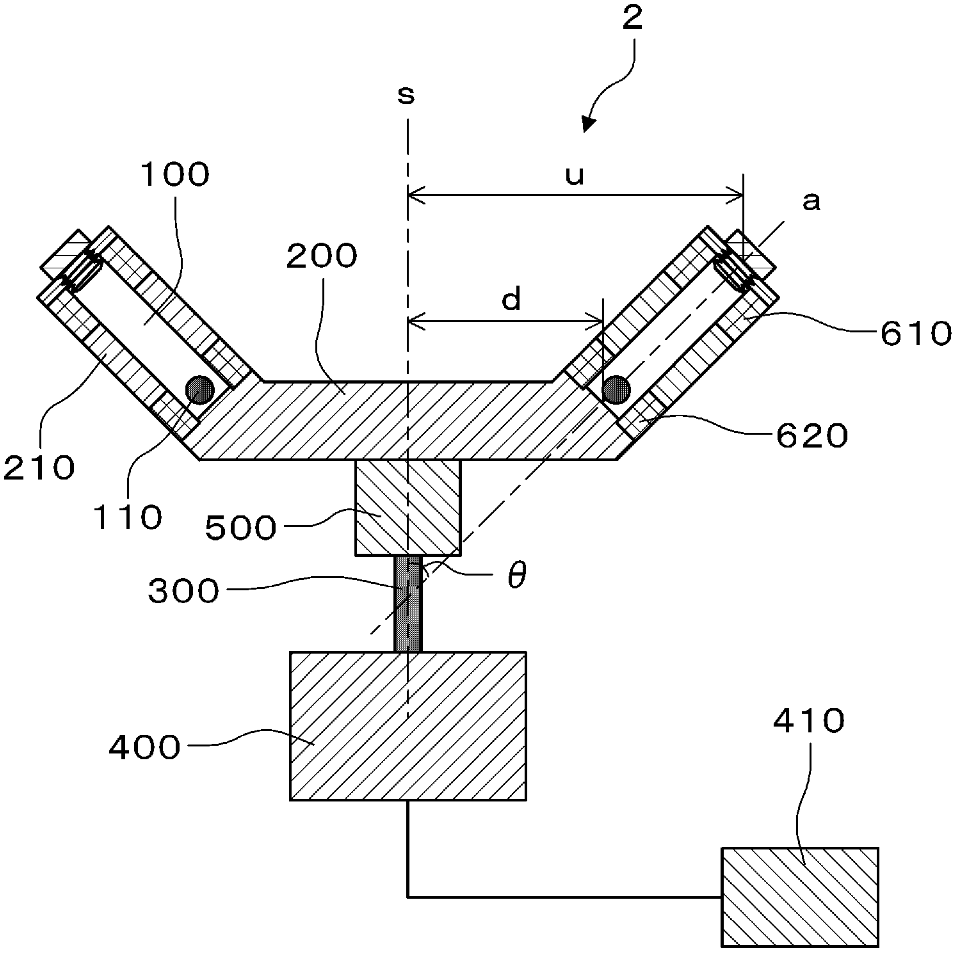
FIG. 1 is a schematic view of a thermal cycler of an embodiment of the invention.
Figure 2:
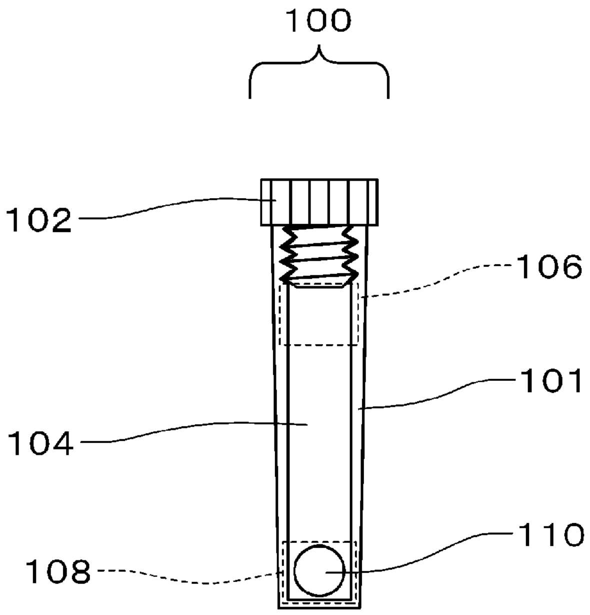
FIG. 2 is a schematic view of a biotip of the embodiment of the invention.
Figure 3:
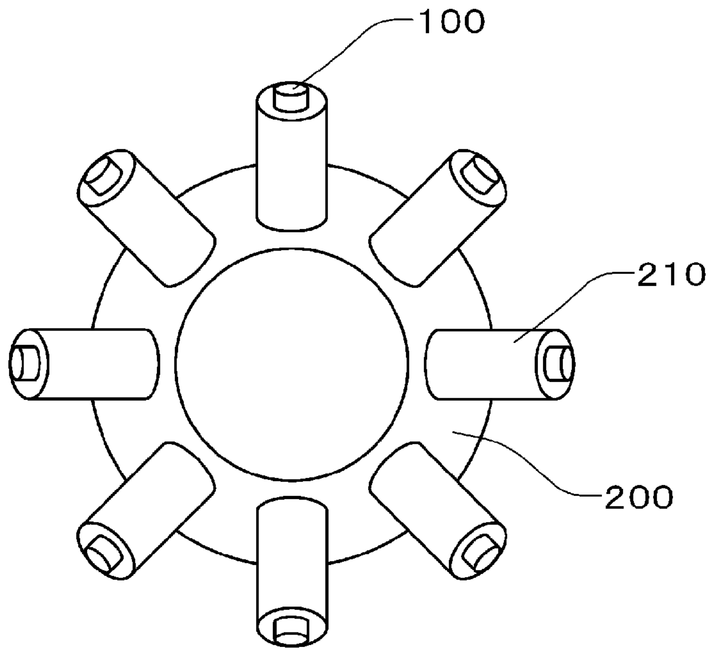
FIG. 3 is a plan view of a rotating unit and a holder of the thermal cycler according to the embodiment of the invention as viewed in the rotational axis direction.

FIG. 1 is a schematic view of a thermal cycler 2 (biological sample reactor) according to an embodiment of the invention, illustrating the state in which biotips (biological sample reaction tips) 100 are attached to a holder 210. FIG. 3 is a plan view of a rotating unit 200 and the holder 210 of the thermal cycler according to the embodiment of the invention as viewed in the rotational axis direction. FIG. 2 is a schematic view of one of the biotips 100 according to the embodiment of the invention. The biotip 100 is used by being attached to the thermal cycler 2 according to the present embodiment. The biotip 100 will be described first with reference to FIG. 2, followed by the thermal cycler 2 with reference to FIGS. 1 and 3.

FIG. 2 is a schematic view of the biotip 100 according to the present embodiment, illustrating the state in which a reaction mixture 110 is stored. The biotip 100 includes a chamber 101, and a cap 102 sealing the chamber 101. The chamber 101 is charged with a liquid 104 immiscible with the reaction mixture 110, and that has a smaller specific gravity than the reaction mixture 110. Preferably, the biotip 100 is formed of resin, for example, such as polypropylene. Use of resin as the material of the biotip 100 enables mass production by injection molding.

As illustrated in FIG. 2, the biotip 100 is formed in such a manner that the reaction mixture 110 moves along the inner wall in proximity thereto between the bottom portion of the biotip 100 (first end portion 108) and the reaction mixture inlet (second end portion 106) sealed with the cap 102. In other words, the second end portion 106 is a region at one end portion of the chamber 101 of the biotip 100, and the first end portion 108 is a region at the other end portion opposite from the second end portion of the chamber 101 of the biotip 100. The biotip 100 is shaped so that the distance between the first end portion 108 and the second end portion 106 is longer than the distance perpendicular to the direction connecting the first end portion 108 to the second end portion 106. Specifically, the direction connecting the first end portion 108 and the second end portion 106 represents the longitudinal direction. The reaction mixture 110 moves along the longitudinal direction of the biotip 100.

The biotip 100 is distributed and stored with the liquid 104 charged into the chamber 101 and sealed with the cap 102. For PCR, a user removes the cap 102, and introduces the reaction mixture 110 containing a sample (potentially with a nucleic acid to be amplified; target nucleic acid) and reagents into the chamber 101 using a micropipette or the like. The chamber 101 is then sealed with the cap 102. Because the liquid 104 charged into the chamber 101 is immiscible with the reaction mixture 110, the reaction mixture 110 forms a droplet in the liquid 104. Further, because the liquid 104 has a smaller specific gravity than the reaction mixture 110, the reaction mixture 110 settles down in the liquid 104, and moves to the lowermost portion of the biotip 100 in the gravitational direction. Specifically, with the biotip 100 held vertically, the reaction mixture 110 moves toward the relatively lower end portion in the gravitational direction. Although the reaction mixture 110 is described as being introduced into the chamber 101 with the reagents, the reaction mixture 110 may be a mixture that results when the reagents applied beforehand to the biotip 100 mix with the liquid (potentially with the target nucleic acid) introduced into the chamber 101.

Preferably, the biotip 100 of the present embodiment is sized to have dimensions with, for example, an inner diameter of about 2 mm, an outer diameter of about 3 mm, and a length of about 30 mm, and stores the reaction mixture 110 of no greater than 2 microliters. When the volume of the reaction mixture 110 exceeds microliters, the diameter of the reaction mixture 110 approaches the inner diameter of the biotip 100. This narrows the space between the reaction mixture 110 and the inner wall of the biotip 100, and interferes with the flow of the liquid 104 above and below the reaction mixture 110, making it difficult for the reaction mixture 110 to move.

Any liquid may be used as the liquid 104 charged into the chamber 101, as long as it does not inhibit PCR, and has a smaller specific gravity than the reaction mixture 110. It is, however, preferable that the liquid 104 have a viscosity of from 3 mPa·s to 10 mPa·s. With the liquid 104 having this viscosity range, the temperature distribution inside the biotip 100 can be stabilized, and the reaction mixture 110 can move in a relatively short time period. When the viscosity of the liquid 104 is below 3 mPa·s, the oil liquid inside the biotip 100 tends to convect under the influence of a heat gradient, and accordingly the temperature distribution inside the biotip 100 tends to become unstable upon application of a centrifugal force to the biotip 100. A viscosity of the liquid 104 above 10 mPa·s makes it difficult for the reaction mixture 110 to move inside the biotip 100, and it takes longer to move the reaction mixture 110. As a result, PCR takes a longer time. Examples of the liquid 104 include mineral oil and silicon oil.

As illustrated in FIG. 1, the thermal cycler 2 according to the present embodiment includes the holder 210, the rotating unit 200, a motor 400 that rotates the rotating unit 200, a support rod 300 that supports the rotating unit 200 and transmits the rotative power of the motor 400 to the rotating unit 200, and a controller 410 that controls the rotation speed of the motor 400. The thermal cycler 2 also includes a first heating unit (heating unit) 620 that heats the first end portion 108 of the biotip 100, a second heating unit 610 that heats the second end portion 106 of the biotip 100, and a slip ring 500 that supplies power to the first heating unit 620 and to the second heating unit 610, and connects the rotating unit 200 to an external power supply.

FIG. 3 is a plan view of the thermal cycler 2 housing a plurality of the biotips 100 according to the present embodiment. FIG. 3 shows a plan view of the thermal cycler 2 as viewed in the rotational axis direction. For example, a total of eight biotips 100 are stored.

The holder 210 may adopt any mechanism, as long as the biotip 100 can be anchored. For example, the holder 210 may be attached to the biotip 100 by being fitted to the first end portion 108 of the biotip 100, or the biotip 100 may be anchored with a belt at the second end portion 106.

Further, the biotip 100 is attached to the holder 210 in such a manner that the distance between the rotational axis s of the rotating unit 200 (described later) and the first end portion 108 of the biotip 100 is shorter than the distance between the rotational axis s of the rotating unit 200 and the second end portion 106 of the biotip 100. In other words, the biotip 100 is attached so that the first end portion 108 is closer to the rotational axis s than the second end portion 106. Further, the biotip 100 is attached to the holder 210 so that the second end portion 106 is higher than the first end portion 108. In other words, the biotip 100 is attached to make the gravitational potential of the first end portion 108 smaller than that of the second end portion 106. With the biotip 100 attached to the holder 210 in this manner, the reaction mixture 110 can move to the second end portion 106 when the centrifugal force created by the rotation of the rotating unit 200 exceeds the gravitational force, and to the first end portion 108 when the centrifugal force is smaller than the gravitational force.

In the example illustrated in FIG. 1, the biotip 100 is attached to the holder 210 by being tilted in such a manner that the distance u to the rotational axis s along the horizontal direction extending from the second end portion 106 of the biotip 100 (the direction orthogonal to the direction of gravitational force) is longer than the horizontal distance d that extends from the first end portion 108 of the biotip 100 to the rotational axis s. Preferably, the biotip 100 may be attached to the holder 210 so that the angle θ created by the straight line a through the second end portion 106 and the first end portion 108 of the biotip 100 and the straight line (rotational axis s) along the vertical direction (the direction of gravitational force) is about 45°. By attaching the biotip 100 with a tilt angle of about 45°, the gravitational force and the centrifugal force can be applied to the reaction mixture 110 most efficiently.

The motor 400 rotates the rotating unit 200 to create a centrifugal force that acts on the biotips 100 attached to the holder 210. Because the holder 210 is part of the rotating unit 200 in the present embodiment, rotating the rotating unit 200 rotates the holder 210. The rotating unit 200 rotates with the rotative power of the motor 400 connected via the support rod 300. The motor 400 can vary the rotation speed according to the output control signal from the controller 410 (described later). In the present embodiment, the rotational axis of the rotating unit 200 is parallel to the direction of gravitational force. The rotational axis may not be necessarily required to be parallel to the direction of gravitational force. As described above, the first end portion 108 and the second end portion 106 are positioned with respect to the rotational axis in such a manner that the first end portion 108 is closer to the rotational axis than the second end portion 106.

The controller 410 controls the rotation speed of the motor 400 by sending a control signal to the motor 400. The controller 410 is not particularly limited, as long as it can freely vary the rotational speed of the motor 400. The controller 410 has at least two modes, as follows. In a first mode, the rotation speed of the motor 400 is controlled so that the rotating unit 200 rotates at a first speed. The first speed is a speed at which the magnitude of the centrifugal force that acts on the biotip 100 (reaction mixture 110) attached to the holder 210 is smaller than the magnitude of the gravitational force that acts on the biotip 100 (reaction mixture 110). The first mode may involve low-speed rotation, or no rotation at all, provided that the gravitational force is greater than the centrifugal force generated by the rotation. In a second mode, the rotation speed of the motor 400 is controlled so that the rotating unit 200 rotates at a second speed. The second speed is a speed at which the magnitude of the centrifugal force that acts on the biotip 100 (reaction mixture 110) attached to the holder 210 is greater than the magnitude of the gravitational force that acts on the biotip 100 (reaction mixture 110). In the second mode, the centrifugal force generated by the rotation is greater than the gravitational force. As is clear from the relationship between the centrifugal force and the gravitational force, the second speed is higher than the first speed. For example, a centrifugal force of about 1.8 G acts on the biotip 100 at three rotations per second with a 5-cm radius of gyration, and thus the centrifugal force is greater than the gravitational force.

The first heating unit 620 heats the first end portion 108 of the biotip 100 attached to the holder 210. On the other hand, the second heating unit 610 heats the second end portion 106 of the biotip 100 attached to the holder 210. The first heating unit 620 and the second heating unit 610 heat the biotip 100 at different temperatures. In other words, the first end portion 108 (lower portion) and the second end portion 106 (upper portion) of the biotip 100 are heated at different temperatures. In the present embodiment, the first end portion 108 of the biotip 100 is heated to about 95° C. by the first heating unit 620, and the second end portion 106 of the biotip 100 is heated to about 60° C. by the second heating unit 610. The heating temperatures of the first heating unit 620 and the second heating unit 610 may be about 60° C. and about 95° C., respectively. Further, the thermal cycler 2 may be configured to include only the first heating unit 620, without the second heating unit 610. In this case, the first heating unit 620 may heat the first end portion 108 to about 95° C., so that the temperature of the second end portion 106 becomes about 60° C. by a temperature gradient as the temperature gradually decreases from the high temperature portion of the first end portion 108 toward the second end portion 106. The first heating unit 620 and the second heating unit 610 may be realized by a heat source, for example, such as a heat wire, that generates heat with the supplied power through the slip ring 500.

1-2. Thermal Cycling Using Thermal Cycler

A thermal cycling method using the thermal cycler 2 according to the present embodiment is described below with reference to FIG. 8.

Figure 8:
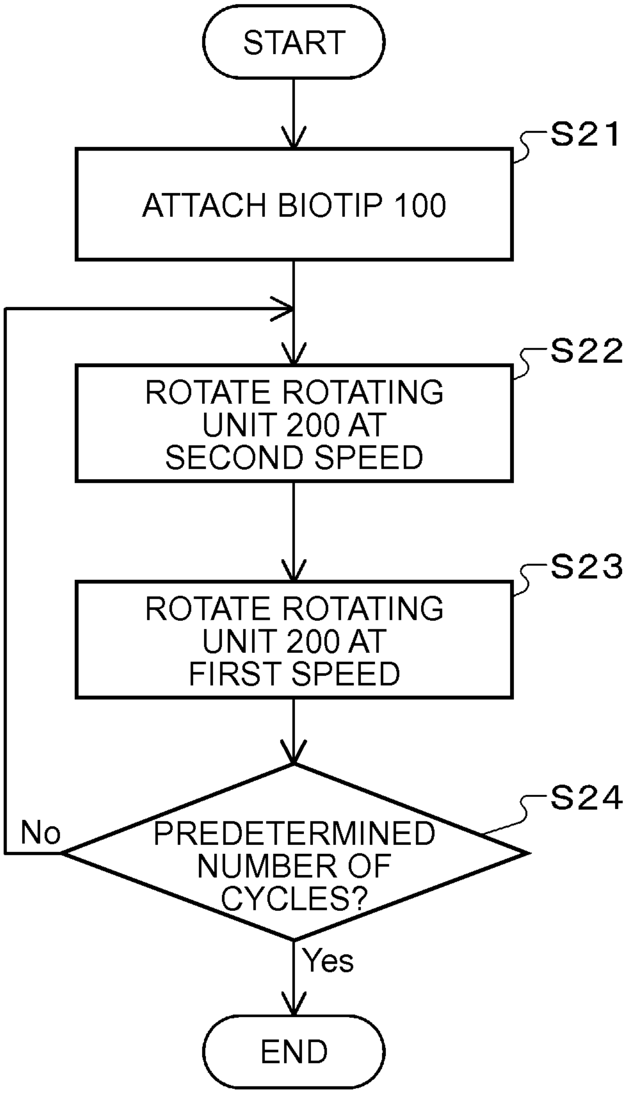
FIG. 8 is a flowchart representing a thermal cycling procedure using the thermal cycler according to the embodiment of the invention.

FIG. 8 is a flowchart representing the procedure of the thermal cycling of the present embodiment. First, the reaction mixture 110 is introduced into the biotip 100 using a micropipette or the like, and the biotip 100 is sealed. After introducing the reaction mixture 110, the biotip 100 is attached to the holder 210 of the thermal cycler 2.

When the rotating unit 200 of the thermal cycler 2 is at rest, the reaction mixture 110 inside the biotip 100 moves to the first end portion 108 by the force of gravity, and stays at the first end portion 108. Because the first end portion 108 has been heated to about 95° C. by the first heating unit 620, the reaction mixture 110 is also heated to about 95° C. For example, the reaction mixture 110 is heated at about 95° C. for 5 seconds when held at the first end portion 108 for about 5 seconds.

Then, the controller 410 is set to the second mode. Specifically, the rotating unit 200 is rotated at the second speed (step S22). While the rotating unit 200 is being rotated at the second speed, the magnitude of the centrifugal force that acts on the biotip 100 (reaction mixture 110) attached to the holder 210 is greater than the magnitude of the gravitational force that acts on the biotip 100 (reaction mixture 110). Accordingly, by the centrifugal force, the reaction mixture 110 in the biotip 100 moves toward the second end portion 106 from the first end portion 108 of the biotip 100. The reaction mixture 110 stays at the second end portion 106 for as long as the rotating unit 200 is rotating at the second speed. Because the second end portion 106 has been heated to about 60° C. by the second heating unit 610, the reaction mixture 110 is also heated to about 60° C. For example, the reaction mixture 110 is heated at about 60° C. for 20 seconds when held at the second end portion 106 for 20 seconds. Thereafter, the controller 410 is set to the first mode. Specifically, the rotation speed of the rotating unit 200 is reduced to rotate the rotating unit 200 at the first speed (step S23). Here, rotating the rotating unit 200 at the first rotation speed includes stopping the rotation of the rotating unit 200. While the rotating unit 200 is being rotated at the first speed, the magnitude of the centrifugal force that acts on the biotip 100 (reaction mixture 110) attached to the holder 210 is smaller than the magnitude of the gravitational force that acts on the biotip 100(reaction mixture 110). Accordingly, the reaction mixture 110 inside the biotip 100 moves toward the first end portion 108 from the second end portion 106 of the biotip 100. The reaction mixture 110 stays at the first end portion 108 for as long as the rotating unit 200 is rotating at the first speed. The reaction mixture 110 is then heated to about 95° C. again.

The reaction mixture 110 can move back and forth between the first end portion 108 and the second end portion 106 inside the biotip 100 by repeating this procedure, specifically, by repeatedly rotating the rotating unit 200 with the controller 410 in the first mode and the second mode. The thermal cycling ends when it is determined that the heating cycle involving the first temperature and the second temperature has reached the predetermined number (step S24). The first end portion 108 and the second end portion 106 are heated at different temperatures by the first heating unit 620 and the second heating unit 610, respectively. Thus, the reaction mixture 110 can be subjected to the thermal cycle by being moved between the first end portion 108 and the second end portion 106. Further, PCR can be stably performed because the heating time of the reaction mixture 110 can easily be controlled by simply switching the rotation speed of the rotating unit 200 with the controller 410.

2. Variations

The invention is not limited to the foregoing embodiment, and various other aspects of the invention are intended to fall within the scope of the invention within the limits of the gist of the invention. Variations of the foregoing embodiment are described below. Note that, in the following descriptions, the same reference numerals are used for elements having the same configurations as those described in the foregoing embodiment, and explanations thereof are omitted.

2-1. Variation 1

Figure 4:
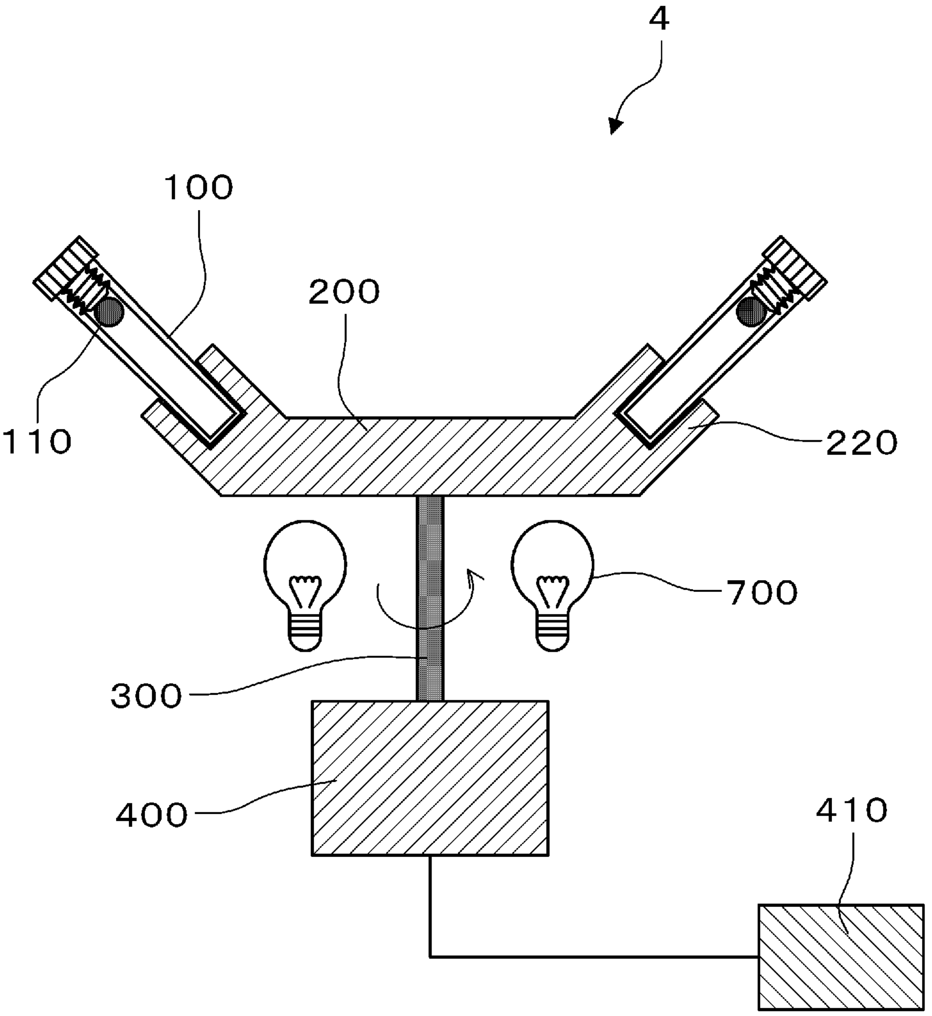
FIG. 4 is a schematic view of a thermal cycler according to Variation 1.

FIG. 4 is a schematic view of a thermal cycler 4 according to Variation 1, illustrating the state in which the rotating unit 200 is rotated with the controller 410 in the second mode. The thermal cycler 4 according to Variation 1 differs from the foregoing embodiment in that a heating lamp (heating unit) 700 is provided instead of the first heating unit 620 and the second heating unit 610 of the thermal cycler 2. The thermal cycler 4 according to Variation 1 also differs from the thermal cycler 2 in the structure of the holder.

As illustrated in FIG. 4, the thermal cycler 4 heats the rotating unit 200 with the heating lamp 700, and utilizes the conducted heat from the rotating unit 200 to heat the first end portion 108 of the biotip 100 attached to the holder 210. The heating lamp 700 is set to such a heating temperature that the first end portion 108 of the biotip 100 is heated to, for example, about 95° C. It is preferable that the rotating unit 200 be formed of metallic material of high conductivity, in order to efficiently transfer heat from the heating lamp 700 to the holder 210. The non-contact heating does not require a configuration such as a slip ring, and can thus simplify the configuration of the thermal cycler.

Further, the thermal cycler 4 illustrated in FIG. 4 has a holder 220 structured to anchor the biotip 100 in the vicinity of the first end portion 108 for the attachment of the biotip 100. Further, the holder 220 is structured so that the second end portion 106 of the biotip 100 is open to the atmosphere inside the thermal cycler 4 (open to the gas inside the thermal cycler 4). For example, the second end portion 106 of the biotip 100 can be heated by maintaining the atmosphere inside the thermal cycler 4 at about 60° C. The atmosphere inside the thermal cycler 4 can be heated by introducing heated gas into the thermal cycler 4 from outside.

With this configuration, the biotip 100 can be heated in a non-contact fashion with the use of the heating lamp. Because no heating mechanism needs to be incorporated in the vicinity of the holder 220, particularly at the second end portion 106 of the biotip 100, the configuration of the apparatus structure can be simplified. Further, because the second end portion 106 of the biotip 100 is open, the fluorescence of the reaction mixture 110 in the real-time fluorescence measurement of a PCR amplified product can be detected from the side of the biotip 100 where there is no obstacle. This enables accurate fluorescence detection with high detection sensitivity.

2-2. Variation 2

Figure 5:
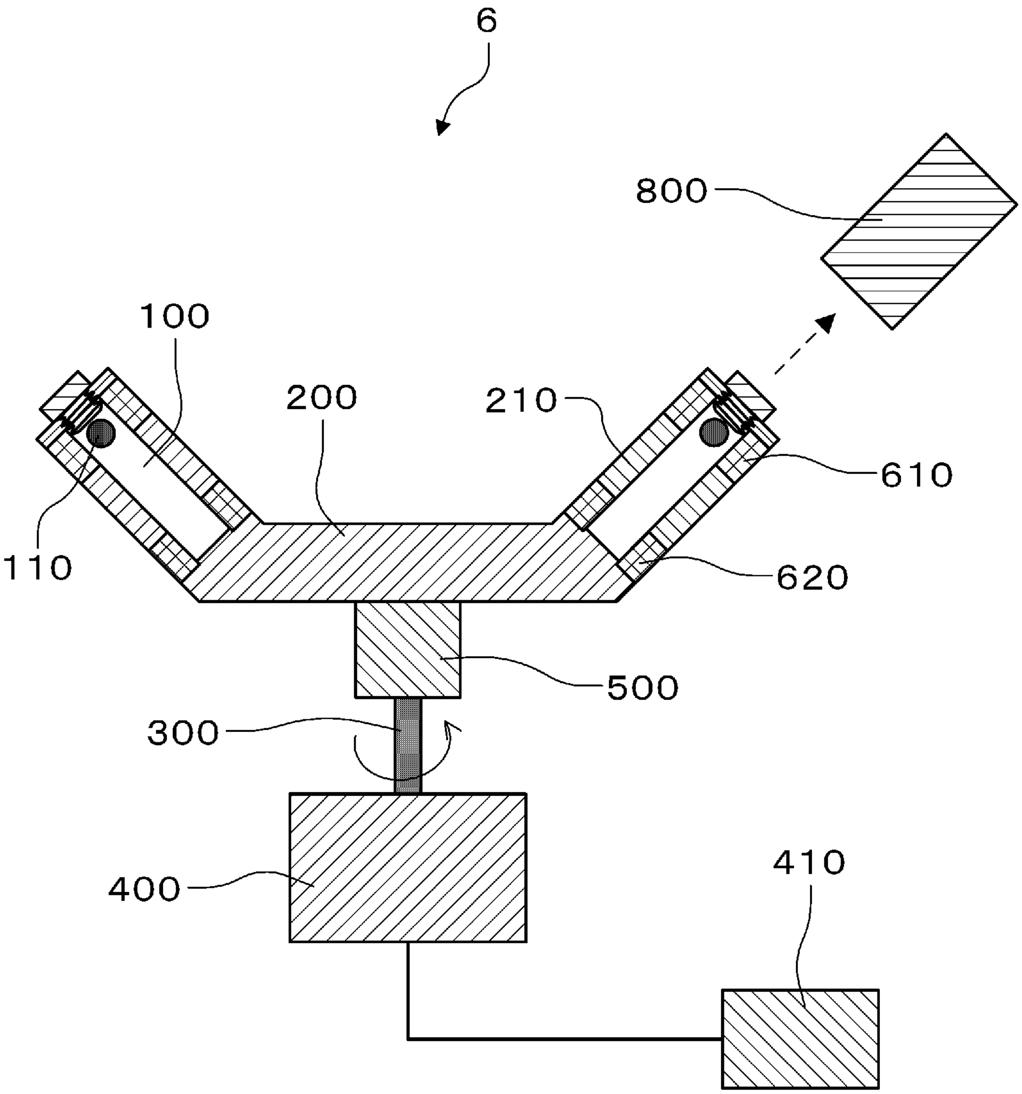
FIG. 5 is a schematic view of a thermal cycler according to Variation 2.

FIG. 5 is a schematic view of a thermal cycler 6 according to Variation 2, illustrating the state in which the rotating unit 200 is rotated with the controller 410 in the second mode. The thermal cycler 6 according to Variation 2 differs from the foregoing embodiment in the addition of a fluorescent detector 800. The thermal cycler 6 according to Variation 2 enables real-time fluorescence detection with a simple structure. The fluorescent detector 800 is disposed above the holder 210. The fluorescent detector 800 shines excitation light on the reaction mixture 110 through the cap 102 of the biotip 100 attached to the holder 210, and detects the excited fluorescence. The fluorescence detection of the reaction mixture 110 is performed while the reaction mixture 110 is in a low-temperature state in the thermal cycle, specifically, while the reaction mixture 110 is held at the second end portion 106 of the biotip 100. The rotating unit 200 is rotating at the second speed while the reaction mixture 110 is being held at the second end portion 106. Thus, fluorescence detection of the reaction mixture 100 is possible for more than one biotip 100 attached to the holder 210, even though the fluorescent detector 800 is anchored in one location. Note that the biotip 100 is preferably formed of a transparent resin, for example, such as polypropylene, because the fluorescence detection is performed from outside of the biotip 100 for the reaction mixture 100 placed inside the biotip 100.

With this configuration, PCR and real-time fluorescence detection can be realized with the thermal cycler 6 of a simple structure. Further, the fluorescence detection of the reaction mixture 110 can be performed for more than one biotip 100 attached to the holder 210, without moving the fluorescent detector 800.

2-3. Variation 3

Figure 6:
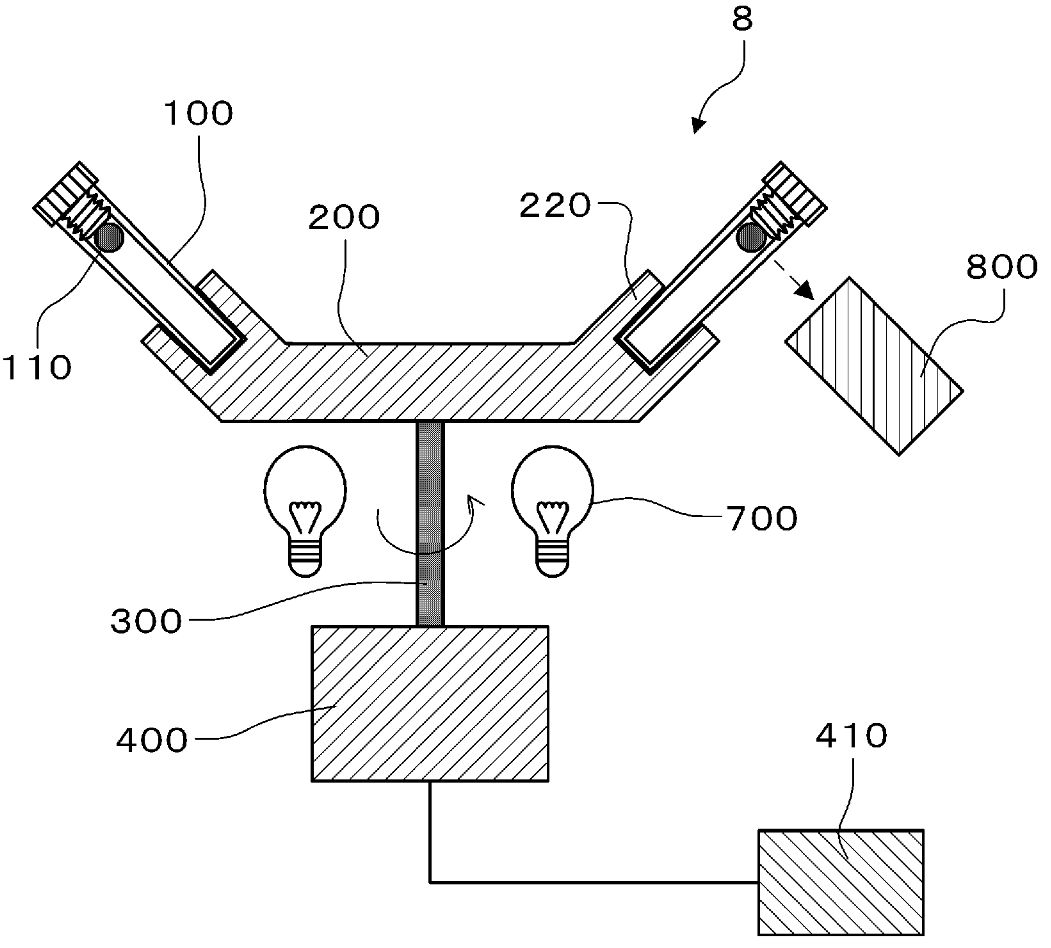
FIG. 6 is a schematic view of a thermal cycler according to Variation 3.

FIG. 6 is a schematic view of a thermal cycler 8 according to Variation 3. The thermal cycler 8 according to Variation 3 is a combination of the configurations of Variations 1 and 2. Specifically, the first end portion 108 of the biotip 100 can be heated in a non-contact fashion with the heating lamp 700. Real-time fluorescence detection is also possible with the use of the fluorescent detector 800.

The thermal cycler 8 illustrated in FIG. 6 differs from Variation 2 in the position of the fluorescent detector 800. Specifically, in contrast to Variation 2 in which the fluorescent detector 800 is disposed above the holder 210 (on the opposite side of the chamber 101 with respect to the cap 102), the fluorescent detector 800 of Variation 3 is disposed on the side of the second end portion 106 of the biotip 100 attached to the holder 220 (along a direction orthogonal to the longitudinal direction of the biotip 100). In the thermal cycler 8, the second end portion 106 of the biotip 100 is open to the atmosphere inside the thermal cycler 8. This enables the fluorescence detection of the reaction mixture 110 held at the second end portion 106 to be performed more freely in terms of detection direction. With the fluorescent detector 800 disposed as illustrated in FIG. 6, excitation light can be shone on the reaction mixture 110 from the side of the biotip 100, and the excited fluorescence can be detected by the fluorescent detector 800. The material on the side of the biotip 100 is thinner than the cap 102 of the biotip 100, and can thus suppress the transmittance of the excitation light and fluorescence from being lowered. This enables more sensitive fluorescence detection.

2-4. Variation 4

Figure 7:
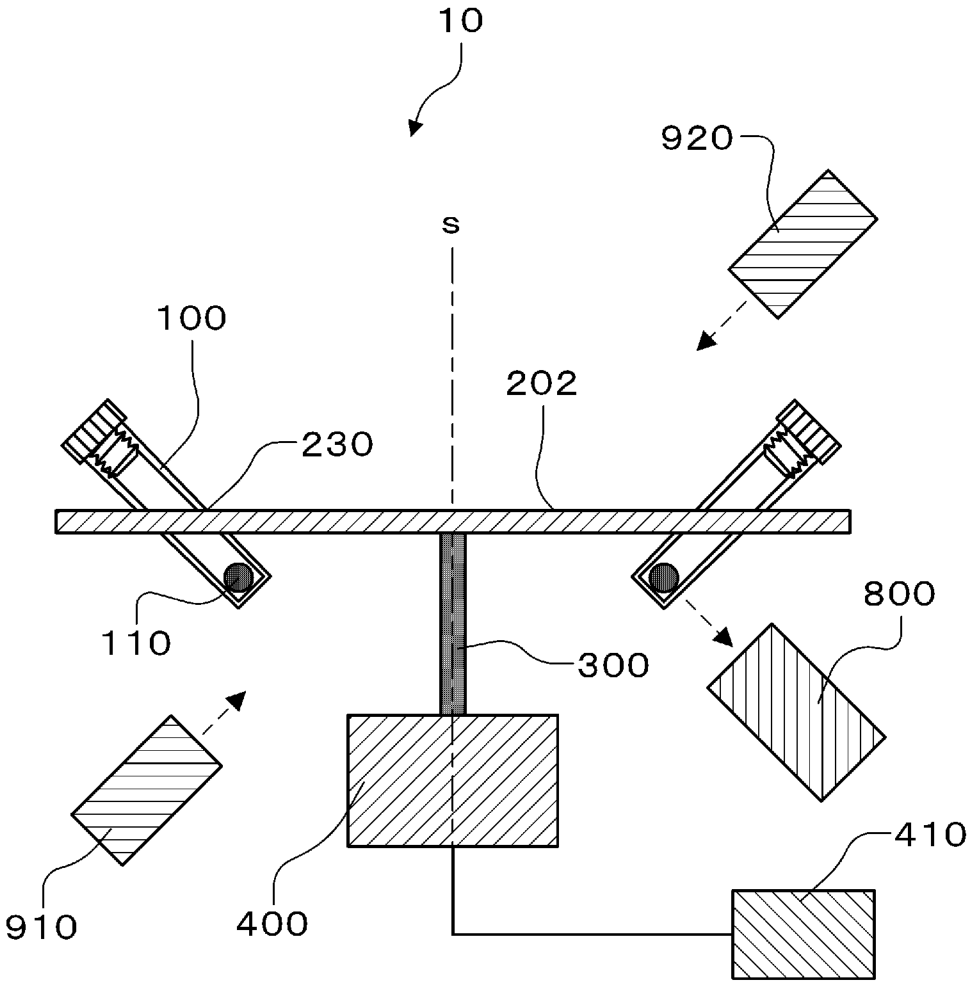
FIG. 7 is a schematic view of a thermal cycler according to Variation 4.

FIG. 7 is a schematic view of a thermal cycler 10 according to Variation 4. The thermal cycler 10 according to Variation 4 differs from the foregoing embodiment in that the holder and rotating unit structures are further simplified, and that the temperature of the atmosphere inside the thermal cycler 10 is controlled to heat the first end portion 108 and the second end portion 106 of the biotip 100.

As illustrated in FIG. 7, the thermal cycler 10 includes a holder 230. The holder 230 anchors the biotip 100 at the middle portion in the longitudinal direction with a belt or the like. In this way, the portions of the biotip 100 in the vicinity of the first end portion 108 and the second end portion 106 become open to the atmosphere inside the thermal cycler 10.

The thermal cycler 10 includes a hot-air blower 910 as a first heating unit, and a hot-air blower 920 as a second heating unit. The hot-air blower 910 heats the atmosphere in the lower portion inside the thermal cycler 10, specifically the atmosphere in the vicinity of the first end portion 108 of the biotip 100 attached to the holder 230, to, for example, about 60° C. The hot-air blower 920 heats the atmosphere in the upper portion inside the thermal cycler 10, specifically the atmosphere in the vicinity of the second end portion 106 of the biotip 100 attached to the holder 230, to, for example, about 95° C. The rotating unit 202 has a board shape with a flat surface perpendicular to the rotational axis s, and holes to which the biotips 100 are attached. In addition to rotating the holder 230, the rotating unit 202 also serves to separate the upper and lower spaces to prevent the upper and lower atmospheres of the thermal cycler 10 from having a uniform temperature. In this way, the second end portion 106 and the first end portion 108 of the biotip 100 can be heated more reliably to about 95° C. and about 60° C., respectively.

Because the first end portion 108 and the second end portion 106 of the biotip 100 are both open in the configuration of the thermal cycler 10 illustrated in FIG. 7, the fluorescence detection of the reaction mixture 110 inside the biotip 100 can be performed from both the first end portion 108 and the second end portion 106. This enables the thermal cycler 10 to be designed more freely. For example, in the thermal cycler 10 illustrated in FIG. 7, the fluorescent detector 800 can be disposed on the side of the first end portion 108, because the reaction mixture 110 is in the low-temperature state in the thermal cycle while the reaction mixture 110 is held at the first end portion 108 of the biotip 100. This makes it possible to further reduce the size of the thermal cycler 10.

What is claimed is:

1. An apparatus comprising:
a biotip having:
a chamber extending in a longitudinal direction axis and being charged with a liquid, the liquid being immiscible with a reaction mixture that has a larger specific gravity than the liquid; and
a cap that seals the chamber; and
a thermal cycler having:
a holder to which the biotip is attached at a predetermined orientation, the holder including a first heating element for heating a first end of the biotip and a second heating element for heating a second end of the biotip;
a rotating unit that rotates the holder; and
a controller that has a first mode and a second mode, the first mode being a setting in which a rotation speed of the rotating unit is set to a first speed at which a magnitude of a centrifugal force that acts on the reaction mixture in the biotip arranged at the predetermined orientation by the rotation of the rotating unit is smaller than a magnitude of a gravitational force that acts on the reaction mixture in the biotip arranged at the predetermined orientation without being rotated, the second mode being a setting in which the rotation speed of the rotating unit is set to a second speed at which the magnitude of the centrifugal force that acts on the reaction mixture in the biotip arranged at the predetermined orientation by the rotation of the rotating unit is greater than the magnitude of the gravitational force that acts on the reaction mixture in the biotip arranged at the predetermined orientation without being rotated.

2. The apparatus according to claim 1, the biotip being formed of a resin.

3. The apparatus according to claim 2, the resin being polypropylene.

4. The apparatus according to claim 1, the biotip having an inner diameter of about 2 mm and a length of about 30 mm.

5. The apparatus according to claim 4, a volume of the reaction mixture being no greater than 2 microliters.

6. The apparatus according to claim 1, a reagent being applied to the biotip.

7. The apparatus according to claim 1, the liquid having a viscosity from 3 mPa·s to 10 mPa·s.

* * * * *